(12) United States Patent
Glickman

(10) Patent No.: US 6,186,146 B1
(45) Date of Patent: Feb. 13, 2001

(54) CANCER TREATMENT METHOD

(76) Inventor: Morton Glickman, 112 Huntington St., New Haven, CT (US) 06551

( * ) Notice: Under 35 U.S.C. 154(b), the term of this patent shall be extended for 0 days.

(21) Appl. No.: 08/782,588

(22) Filed: Jan. 13, 1997

Related U.S. Application Data

(63) Continuation-in-part of application No. 08/706,186, filed on Aug. 30, 1996, now abandoned.

(51) Int. Cl.$^7$ .................................................. A61B 19/00
(52) U.S. Cl. ................................. 128/898; 604/4; 604/5
(58) Field of Search ................................ 128/898; 604/4, 604/5, 101, 96, 98; 606/192, 108, 194

(56) References Cited

U.S. PATENT DOCUMENTS

| Re. 28,742 | 3/1976 | Rafferty et al. . |
|---|---|---|
| 2,642,874 | 6/1953 | Keeling . |
| 3,045,677 | 7/1962 | Wallace . |
| 3,411,506 | 11/1968 | Velasco . |

(List continued on next page.)

FOREIGN PATENT DOCUMENTS

| 28 34 956 | 2/1980 | (DE) . |
|---|---|---|
| 0 119 596 | 9/1984 | (EP) . |
| 0 185 865 | 7/1986 | (EP) . |
| 0 228 532 | 7/1987 | (EP) . |
| 511951 | 6/1976 | (SU) . |
| 651 817 | 3/1979 | (SU) . |
| WO 88/06045 | 8/1988 | (WO) . |

OTHER PUBLICATIONS

Turk et al. "Isolated Pelvic Perfusion for Unresectable Cancer Using a Balloon Occlusion Technique" Arch Surg 128:533–539, May 1993.*

Ku et al. "Direct Hemoperfusion Under Infrahepatic Inferior Vena Cava Isolation for the Intraarterial Chemotherapy of Pelvic Tumors" Jpn J Surg24:1031–1033, 1994.*

Wanebo et al. "Preoperative Therapy for Advanced Pelvic Malignancy by Isolated Pelvic Perfusion with the Baloon–Occlusion Technique" Ann Surg Oncol 3(3):295–303, 1996.*

(List continued on next page.)

Primary Examiner—Mickey Yu
Assistant Examiner—Kelly O'Hara
(74) Attorney, Agent, or Firm—Stephen E. Feldman

(57) ABSTRACT

An in situ treatment of an organ, such as a kidney, of a living body, having a disease or tumor. The method includes: subjecting a diseased or tumorous organ, such as a kidney, to an effective amount of a therapeutic agent, by infusing the agent via blood entering the organ, creating an isolated section in a major vein spanning the area where the tributary veins connect with the major vein, the major vein and tributary veins being directly associated with the organ; passing contaminated effluent blood from the tributary veins of the organ to the isolated section and capturing the effluent blood therein; and, evacuating the captured blood from the isolated section without exposing the contaminated effluent blood to other organs or tissues of the body and without interrupting the general circulation in the system of the body.

6 Claims, 3 Drawing Sheets

U.S. PATENT DOCUMENTS

| | | |
|---|---|---|
| 3,516,408 | 6/1970 | Montanti . |
| 3,647,324 | 3/1972 | Rafferty et al. . |
| 3,811,800 | 5/1974 | Shill . |
| 3,837,347 | 9/1974 | Tower . |
| 3,851,649 | 12/1974 | Villari . |
| 3,864,055 | 2/1975 | Kletschka et al. . |
| 3,888,250 | 6/1975 | Hill . |
| 3,957,389 | 5/1976 | Rafferty et al. . |
| 3,959,128 | 5/1976 | Harris . |
| 3,970,408 | 7/1976 | Rafferty et al. . |
| 3,995,617 | 12/1976 | Watkins et al. . |
| 4,013,564 | 3/1977 | Nose . |
| 4,037,984 | 7/1977 | Rafferty et al. . |
| 4,047,526 | 9/1977 | Reynolds et al. . |
| 4,048,064 | 9/1977 | Clark, III . |
| 4,059,512 | 11/1977 | Harris . |
| 4,127,481 | 11/1978 | Malchesky et al. . |
| 4,140,652 | 2/1979 | Korshak et al. . |
| 4,171,283 | 10/1979 | Nakashima et al. . |
| 4,183,811 | 1/1980 | Walch et al. . |
| 4,192,302 | 3/1980 | Boddie . |
| 4,206,050 | 6/1980 | Walch et al. . |
| 4,218,321 | 8/1980 | Sasaki et al. . |
| 4,231,366 | 11/1980 | Schael . |
| 4,250,141 | 2/1981 | Lehmann et al. . |
| 4,300,550 | 11/1981 | Gandi et al. . |
| 4,300,551 | 11/1981 | Kinney . |
| 4,303,521 | 12/1981 | Lehmann . |
| 4,313,831 | 2/1982 | Lehmann et al. . |
| 4,376,707 | 3/1983 | Lehmann . |
| 4,385,631 | 5/1983 | Uthmann . |
| 4,416,280 | 11/1983 | Carpenter et al. . |
| 4,423,725 | 1/1984 | Baran et al. . |
| 4,445,892 | 5/1984 | Hussein et al. . |
| 4,500,309 | 2/1985 | Diederich et al. . |
| 4,540,402 | 9/1985 | Aigner . |
| 4,546,759 | 10/1985 | Solar . |
| 4,563,170 | 1/1986 | Aigner . |
| 4,573,966 | 3/1986 | Weikl et al. . |
| 4,609,461 | 9/1986 | Takata et al. . |
| 4,610,662 | 9/1986 | Weikl et al. . |
| 4,634,604 | 1/1987 | Tlustakova et al. . |
| 4,636,195 | 1/1987 | Wolinsky . |
| 4,648,865 | 3/1987 | Aigner . |
| 4,655,746 | 4/1987 | Daniels et al. . |
| 4,666,426 | 5/1987 | Aigner . |
| 4,681,764 | 7/1987 | Endo et al. . |
| 4,696,668 | 9/1987 | Wilcox . |
| 4,705,502 | 11/1987 | Patel . |
| 4,708,718 | 11/1987 | Daniels . |
| 4,714,460 | 12/1987 | Calderon . |
| 4,728,432 | 3/1988 | Sugiyama et al. . |
| 4,731,055 | 3/1988 | Melinyshyn et al. . |
| 4,741,328 | 5/1988 | Gabbay . |
| 4,744,366 | 5/1988 | Jang . |
| 4,781,677 | 11/1988 | Wilcox . |
| 4,820,261 | 4/1989 | Schmoll et al. . |
| 4,828,882 | 5/1989 | Tsezos et al. . |
| 4,832,034 | 5/1989 | Pizziconi et al. . |
| 4,832,839 | 5/1989 | Tamura . |
| 4,867,742 | 9/1989 | Calderon . |
| 4,883,459 | 11/1989 | Calderon . |
| 4,897,189 | 1/1990 | Greenwood et al. . |
| 4,897,200 | 1/1990 | Smakman . |
| 4,911,163 * | 3/1990 | Fina ................................ 606/127 |
| 4,913,701 | 4/1990 | Tower . |
| 4,955,857 | 9/1990 | Shettigar . |
| 4,959,148 | 9/1990 | Clark, III . |
| 4,988,569 | 1/1991 | Okazaki et al. . |
| 5,002,559 | 3/1991 | Tower . |
| 5,004,455 | 4/1991 | Greenwood et al. . |
| 5,021,045 | 6/1991 | Buckberg et al. . |
| 5,028,339 | 7/1991 | Clark, III . |
| 5,033,998 | 7/1991 | Corday et al. . |
| 5,047,180 | 9/1991 | Steiner et al. . |
| 5,051,185 | 9/1991 | Watanabe et al. . |
| 5,064,949 | 11/1991 | Steiner et al. . |
| 5,069,662 * | 12/1991 | Bodden ................................ 604/4 |
| 5,084,031 | 1/1992 | Todd et al. . |
| 5,087,247 | 2/1992 | Horn et al. . |
| 5,102,390 | 4/1992 | Crittenden et al. . |
| 5,106,363 | 4/1992 | Nobuyoshi . |
| 5,120,323 | 6/1992 | Shockey et al. . |
| 5,122,115 | 6/1992 | Marks . |
| 5,129,883 | 7/1992 | Black . |
| 5,135,474 | 8/1992 | Swan et al. . |
| 5,135,484 | 8/1992 | Wright . |
| 5,158,540 | 10/1992 | Wijay et al. . |
| 5,161,547 | 11/1992 | Tower . |
| 5,161,773 | 11/1992 | Tower . |
| 5,163,910 | 11/1992 | Schwartz et al. . |
| 5,167,622 | 12/1992 | Muto . |
| 5,167,623 | 12/1992 | Cianci et al. . |
| 5,178,608 | 1/1993 | Winters . |
| 5,186,712 | 2/1993 | Kelso et al. . |
| 5,188,595 | 2/1993 | Jacobi . |
| 5,200,181 | 4/1993 | Soltys et al. . |
| 5,209,239 | 5/1993 | Watanabe et al. . |
| 5,209,717 | 5/1993 | Schmoll et al. . |
| 5,209,723 | 5/1993 | Twardowski et al. . |
| 5,211,849 | 5/1993 | Kitaevich et al. . |
| 5,226,427 | 7/1993 | Buckberg et al. . |
| 5,236,417 | 8/1993 | Wallis . |
| 5,254,089 | 10/1993 | Wang . |
| 5,279,546 | 1/1994 | Mische et al. . |
| 5,281,200 | 1/1994 | Corso, Jr. et al. . |
| 5,286,259 | 2/1994 | Ganguly et al. . |
| 5,304,121 | 4/1994 | Sahatjian . |
| 5,312,344 | 5/1994 | Grinfeld et al. . |
| 5,324,261 | 6/1994 | Amundson et al. . |
| 5,338,301 | 8/1994 | Diaz . |
| 5,360,403 | 11/1994 | Mische . |
| 5,370,614 | 12/1994 | Amundsen et al. . |
| 5,397,307 | 3/1995 | Goodin . |
| 5,397,310 | 3/1995 | Chu et al. . |
| 5,398,687 | 3/1995 | Abell . |
| 5,405,320 | 4/1995 | Twardowski et al. . |
| 5,411,479 * | 5/1995 | Bodden ................................ 604/98 |
| 5,423,745 | 6/1995 | Todd et al. . |
| 5,458,583 | 10/1995 | McNeely et al. . |
| 5,460,610 | 10/1995 | Michael . |
| 5,462,529 | 10/1995 | Simpson et al. . |
| 5,489,274 | 2/1996 | Chu et al. . |
| 5,505,698 | 4/1996 | Booth et al. . |
| 5,509,897 | 4/1996 | Twardowski et al. . |
| 5,569,182 | 10/1996 | Twardowski et al. . |
| 5,597,377 | 1/1997 | Aldea . |
| 5,609,598 | 3/1997 | Laufer et al. . |
| 5,728,066 | 3/1998 | Daneshvar . |

OTHER PUBLICATIONS

Wizemann et al., Portocaval Hemofiltration During the Anhepatic Phase in Isolated Liver Perfusion, pp. 485–487.

Galletti et al., Hemodialysis in Cancer Chemotherapy, pp. 20–24.

Horton et al., Continuous Arteriovenous Hemofiltration: An Alternative to Hemodialysis, pp. 1361–1368.

Kamidono et al., A Fundamental Study of Regional Chemotherapy Given by Intraarterial Infusion with Concomitant Hemodialysis and Hemoperfusion, pp. 176–178.

Winchester et al., Dialysis and Hemoperfusion of Poison and Drugs, pp. 787–791.

Nose et al., Therapeutic Apheresis: A Critical Look, pp. 93–125, 171–175.

Ausman, Development of a Technic for Isolated Perfusion of the Liver, pp. 3993–3997.

Aigner et al., First Experimental and Clinical Results of Isolated Liver Perfusion with Cytotoxics in Metastases from Colorectal Primary, pp. 99–102.

Tani et al., New Anticancer Treatment by Hemoperfusion with Endotoxin Immobilized Fiber, pp. 202–217, 236–240.

Curley et al., Hepatic Arterial Infusion Chemotherapy with Complete Hepatic Venous Isolation and Extracorporeal Chemofiltration: A Feasibility Study of a Novel System, pp. 175–183.

Beheshti et al., Percutaneous Isolated Liver Perfusion for Treatment of Hepatic Malignancy, JVIR 3:453–458.

Curley et al., Reduction of Systemic Drug Exposure After Hepatic Arterial Infusion of Doxorubicin with Complete Hepatic Venous Isolated and Extracorporeal Chemofiltration, Surgery 114:579–585.

Curley et al., Increased Doxorubicin Levels in Hepatic Tumors with Reduced Systemic Drug Exposure Achieved with Complete Hepatic Venous Isolation and Extracorporeal Chemofiltration, Cancer Chemother Pharmacol 33:251–257.

Ravikumar et al., Percutaneous Hepatic Vein Isolation and High Dose Hepatic Arterial Infusion Chemotheraphy for Unresectable Liver Tumors, J Clin Oncol 12(12):2723–2736.

August et al, Pharmacokinetic Evaluation of Percutaneous Hepatic Venous Isolation for Administration of Regional Chemotherapy, Surg Oncol 4:205–216.

Ku et al., Induction of Long–Term Remission in Advanced Hepatocellular Carcinoma with Percutaneous Isolated Liver Chemoperfusion, Ann Surg 227:519–526.

Ku et al., Single Catheter Technique of Hepatic Venous Isolation and Extracorporeal Charcoal Hemoperfusion for Malignant Liver Tumors, American Journal of Surgery 173:103–109.

Ku et al., Clinical Pilot Study on High–Dose Intraarterial Chemotherapy with Direct Hemoperfusion Under Hepatic Venous Isolation in Patients with Advanced Hepatocellular Carcinoma, Surgery 117:510–519.

Ku et al., Extracorporeal Removal of Anticancer Drugs in Hepatic Artery Infusion: The Effect of Direct Hemoperfusion Combined with Venovenous Bypass, Surgery 107;273–281.

ku et al, Percutaneous Technique of HVI and Charcoal Hemoperfusion with a Dual–Balloon Vena Cava Catheter, Surgery 116(3):360.

Curley et al., HAI Chemotherapy With Complete and Extracorporeal Chemofiltration, Anti–Cancer Drugs 2;175–183.

\* cited by examiner

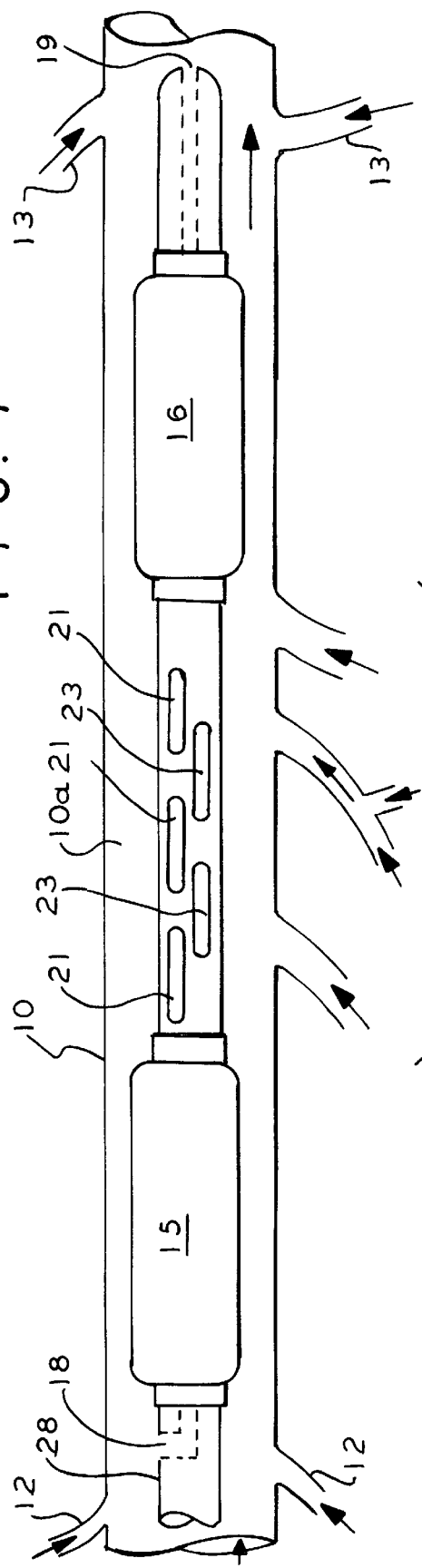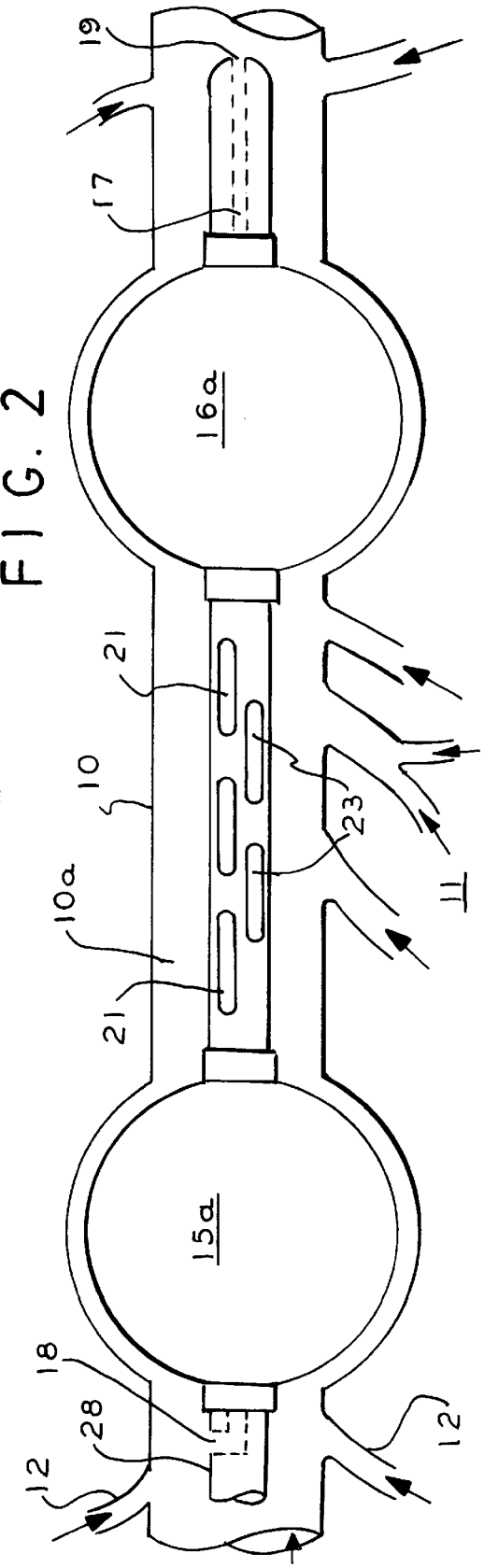

CANCER TREATMENT METHOD

This application is a continuation-in-part of Ser. No. 08/706,186 filed Aug. 30, 1996 now abandoned.

FIELD OF THE INVENTION

The present invention is directed to a method for treating an organ of the body afflicted with a disease or tumor by isolating the diseased organ from the general circulation system of the body and treating the afflicted organ in situ without affecting other organs and/or tissues of the host body. In particular, the present invention is directed to a method for treating an isolated disease in an organ of the body, such as a tumor of the kidney, where a therapeutic agent is infused into the diseased organs through the blood supplying that organ and contained therein while eliminating contaminated blood from the organ and maintaining essentially normal blood circulation throughout the host body.

BACKGROUND OF THE INVENTION

Current acceptable medical practice for treating cancer in an organ involves surgical removal of the afflicted organ. In the case of kidney tumors, for example, the afflicted kidney is surgically removed, especially if the tumor is malignant. Statistically, a relatively small percentage—estimated at about 20 to about 30 percent—of patients subject to surgical removal of a tumorous kidney experience sustained, favorable response to this form of therapy. A majority of patients in this category terminate from metastatic (secondary) cancer occurring outside the kidney. If persons suffering from kidney cancer are not permanently benefitted, additional or alternative modes of therapy requiring more radical procedures will have to be developed to act more effectively with the disease at its first presentation so that surgical removal of a diseased organ will not be the only acceptable treatment.

Some organ malignancies have been treated with toxic agents in situ. Some kidney malignancies, for example, have been treated with chemotherapeutic agents and biological agents which are toxic moieties derived from organic sources. However, as with some chemotherapeutic agents, biological agents can not be introduced into the general circulation of the host body in sufficient strength and/or quantity to achieve satisfactory therapeutic response in the diseased organ because their negative, toxic effects on other organs and tissues of the host body rival their positive, therapeutic effect in the diseased organ.

The majority of kidney cancer patients die from metastatic disease. One promising method of treatment involves encouraging the growth of immune cells; i.e., Tumor Infiltrating Lymphocytic cells (TIL cells), within the kidney to attack metastatic tumors. The goal of this treatment is to shrink the kidney tumor prior to removing the kidney.

Another therapeutic procedure for organs with local tumors, sucl as the kidney, includes the surgical removal of tumorous matter from the organ an cultivating TIL cells in sufficient quantity for infusion into the patient for therapeutic treatment of metastatic tumors. The cultured cells may react favorably against both the primary tumor cells and any metastatic cancer cells in the body. However, time is needed in order to cultivate a sufficient quantity of such cells for adequate and effective treatment of a patient and the patient may not have the time required for such cultivation.

In general, treating diseased or tumorous organs with chemotherapeutic agents has not had a dramatic impact. Although certain drugs and biological agents have exhibited considerable activity in some treatment protocols, their effects have been negated by systemic toxicity.

A process for treating a diseased liver by profusing a high concentration of a therapeutic agent through the liver is disclosed in U.S. Pat. No. 5,069,662 to Bodden, et. al. This process includes percutaneously inserting a double balloon catherer into the inferior vena cava of the liver to prepare for delivery of blood flowing between the liver and the heart. A therapeutic agent is fed into the liver through the arterial blood flowing into the liver. The blood vessels carrying blood from the liver are blocked by inflating the balloons in the catherer to prevent contaminated blood from entering the general circulation of the body. The venous blood from the liver contaminated with the therapeutic agent is then withdrawn from the body. The balloons in the double balloon catherer are positioned to span the exit vessels through which blood flows coming out of the liver and are expanded to block the vessel above and below the exit vessels thereby effectively isolating the blood flowing from the treated liver. Contaminated blood is removed from the body through an opening in a lumen provided within the catherer between the expanded balloons. The blood is treated to remove contamination and the cleaned, detoxified blood is then returned to the general circulation of the body.

SUMMARY OF THE INVENTION

The present invention provides a method for treating a disease by stimulating a response in an organ of the body, such as a kidney, in situ in which a therapeutic agent is infused into the organ via the blood entering the organ and in which the blood containing the therapeutic agent is recovered from the organ and removed before the blood enters the general circulation system of the body. This is uniquely accomplished by blocking a section of a major vein without interrupting the flow of blood through the major vein and through the general circulation system of the body.

Thus, the process of the invention provides for the in situ treatment of an organ of the body having a disease or tumor and generally comprises: subjecting an organ of the body having a disease or tumor to an effective amount of a therapeutic agent by infusing said agent via blood entering said organ; creating an isolated section in a major vein spanning the area where the tributary veins connect with said major vein, said major vein and said tributary veins being directly associated with said organ; passing contaminated, effluent blood from said tributary veins of said organ to said isolated section and capturing said effluent blood therein; and, evacuating said captured blood from said isolated section without exposing said contaminated, effluent blood to other organs or tissues of said body and without interrupting the general blood circulation of said body.

A significant and important advantage of the process of the invention over other procedures is that the toxicity or strength of the therapeutic agent used on the diseased or tumorous organ is limited only by the level of therapeutic agent that the treated organ can withstand rather than the adverse affect that the therapeutic agent may have on other organs and/or tissues of the body. Equally significant and important is the fact that blood flowing from the treated organ and contaminated with the therapeutic agent can be isolated, removed and withdrawn from the body, detoxified and cleansed, and returned to the body without interfering with, disrupting, interrupting, or stopping the normal circulation of blood flowing through the body.

As mentioned above, treatment of diseases and tumors of body organs, especially the kidneys, by many currently acceptable medical procedures involves surgical removal of tumors from the patient, culturing the lymphocyte cells infiltrating the tumors (Tumor Infiltrating Lymphocytes, or "TIL" cells) to grow an adequate number of the TIL cells, and potentiating the cytolytic activity of these cells prior to infusing them into a patient as a form of treatment.

This treatment requires that an adequate amount of IL-2 be used in the culture medium in order to expand and activate the TIL cells. Typically, it takes from about four to about six weeks to grow a sufficient amount of cells to treat a patient. Once a sufficient amount of cells are grown ex vivo, they are collected in a transfusion device for delivery to a patient. As patients receive a TIL cell infusion, they also receive bolus injections of IL-2 every eight hours for five days. This kind of therapy is commonly known as TIL/IL-2 therapy.

TIL/IL-2 therapy often fails because it is not always possible to grow a sufficient amount of cells ex vivo to treat the patient(s). Cell growth is a labor intensive and expensive procedure and failure can occur for many reasons relating to the growth conditions, the most common cause being contamination of the cell culture. Since culturing cells is time consuming, labor intensive and costly, each step of the culturing process increases the likelihood of contamination and ultimate failure. When cells fail to grow or become contaminated, at least two months of effort can easily be lost thereby delaying therapy and often discouraging a patient from undergoing a second attempt.

By using the process of the present invention, TIL/IL-2 therapy is improved as the process permits IL-2 to be delivered directly to the diseased area or tumor within the patient rather than removing the diseased area or tumor from the patient for ex vivo culturing. By infusing high doses of IL-2 directly to a diseased or tumorous organ such as a kidney, the patient is spared from undergoing a surgical procedure to remove a diseased area or tumor; avoids the side effects of any administered therapy, especially the risk of infection; eliminates potential failure of cell proliferation in culture; and, does not have any time delay in administering the therapy; i.e., waiting four to six weeks to grow a sufficient population of cells. Thus, the process of the invention enhances the anti-tumor activity of the host immune system to fight a tumor. This anti-tumor response in the kidney will not only be against the primary tumor in the kidney, but any metastases outside the tumor as well.

Another advantage of the process of the invention arises from the fact that the kidney is the primary filter for most biologicals. Biologicals are agents typically produced from recombinant DNA techniques and include such agents as the interleukins and the interferons, among others. As with chemotherapeutics, most biologicals can not be administered at sufficiently high doses to achieve desirable therapeutic responses. Biologicals are particularly effective for treating chemotherapy-resistant tumors which include renal cell carcinoma, melanoma, hepatoma, and sarcoma. The significance of this for an affected kidney (i.e., renal cell carcinoma) is that the kidney and will filter out excess amounts of these biologicals through normal tubule clearance and, therefor, tolerates these agents well.

However, if these biological drugs are administered systemically to a patient, they will induce diffuse capillary leak syndrome which leads to intravascular fluid escaping from the bloodstream and damaging the patient's vital organs. This can potentially cause heart failure, lungs filling with fluid, and coma. By using the process of the invention to deliver these drugs directly to the kidney, a large portion of these biologicals will either achieve their intended therapeutic effect; i.e., activate an immune response, or be removed from the blood stream by the combined filtration actions of the kidney and that included in the present invention.

A further advantage arising out of using IL-2 to treat the kidney is that it will enable a physician to determine whether or not a patient should undergo removal of a kidney. The only currently known curative therapy for early stages of kidney cancer involves removal of the tumorous kidney. Unfortunately, only 20 to 30 percent of the patients respond to this therapy and they will eventually die from metastatic cancer. Physicians try to avoid surgery if the patient will eventually die despite removal of the tumorous kidney as they are reluctant to subject patients to major surgery and a long recovery time if it will not significantly reduce their pain nor lengthen their lives.

By using the process of the invention to deliver IL-2 directly to the kidney, a physician will be able to observe whether the tumor is responding to treatment while reducing the debilitating effects of highly toxic IL-2 therapy. This response is predictive of the response of the metastases. Since the process of the invention is minimally invasive, physicians will prefer to treat patients with it first before considering alternative therapy. Those patients that do not respond when treated through the process of the invention can be dealt with in a humane manner avoiding unnecessary and debilitating surgery.

The present invention provides for inserting a catheter into an artery feeding blood to the organ to be treated and infusing a therapeutic agent into the organ through the blood flowing into the organ. The catheter used to deliver the therapeutic agent to the organ can be a catheter normally used for such medical procedures. A second catheter consisting of a double balloon catheter having two, spaced, inflatable balloons is inserted into a major vein of the circulation system and positioned in the major vein so that the spaced balloons of the double balloon catheter span that portion or section of the major vein where the tributary veins coming from the organ on which the procedure is to be applied connect with the major vein. The spaced balloons of the second catheter are inflated so that they contact the interior wall of the major vein thus forming two, spaced blocks or plugs which effectively block the spanned portion of the major vein. This creates an isolated or contained section in the major vein in which blood entering the major vein from the treated organ can be captured and isolated from the remainder of the circulation system.

The process of the invention also provides for a by-pass which shunts the blood flowing in a major vein through and past the section of the major vein blocked by the two, spaced inflated balloons enabling blood to continuously flow through the major vein while blood flowing into the major vein from the organ being treated with a therapeutic agent is isolated and contained in the blocked section. This by-pass serves as an internal conduit or lumen within the double balloon catheter and its ends extend and protrude beyond the extremities of the double balloon portion of the catheter. Each of the protruding ends of the internal lumen or conduit has an opening formed therein, one of which is anterior (or cephalod) to and the other of which is posterior (or cauded) of the isolated or contained section created by the spaced, inflatable balloons.

Just before or concurrently with inflating the balloons of the double balloon catheter positioned in the major vein, the blood shunt or by-pass can be opened to provide a path around the blockages created by the inflated balloons so that normal flow of blood continues through the major vein without interruption.

Blood flowing from the treated organ into the isolated section created between the inflated balloons containing a contaminating therapeutic agent is evacuated from the isolated section through one or more internal conduits or lumens contained in the double balloon catheter and positioned therein between the two, spaced balloons. These internal conduits or lumens are provided with a plurality of openings formed therein and their ends also extend and protrude beyond the ends of the double balloon catheter. Contaminated blood enters the internal conduits or lumens through the openings formed therein and is evacuated from the isolated or contained section between the inflated balloons in the major vein through a protruding end of the internal conduits or lumens. The protruding ends of the internal conduits or lumens are connected to a blood cleansing device which removes the contaminating therapeutic agent from the blood and returns the cleansed and detoxified blood back to the circulation system of the body.

Detoxification and cleansing of the contaminated blood can be accomplished by means and techniques commercially available to medical practioners. Illustrative of such means and techniques are hemoperfusion cartridges, hemodialysis, hemofiltration, and hemoadsorption through antibodies or biological ligands or molecules capable or rendering them non-toxic and/or clearing the blood of the therapeutic agent and allowing the patient's own detoxified and cleaned blood to be re-administered to the patient.

Representative devices for detoxifying and cleansing contaminated blood and recirculating the cleaned blood back into a patient's normal circulation system are disclosed in U.S. Pat. Nos. 4,362,155; 4,637,880; and, 4,820,261 among others.

BRIEF DESCRIPTION OF THE DRAWING

The process of the invention will become more apparent from the ensuing description when considered together with the accompanying drawing wherein:

FIG. 1 is a side view illustrating the head end part of a double balloon catheter and internal blood shunt shown with the balloons in an uninflated condition positioned in a blood vessel;

FIG. 2 is the same side view as in FIG. 1 showing the balloons in an inflated condition;

DETAILED DESCRIPTION OF THE DRAWING AND THE INVENTION

Figure 3:
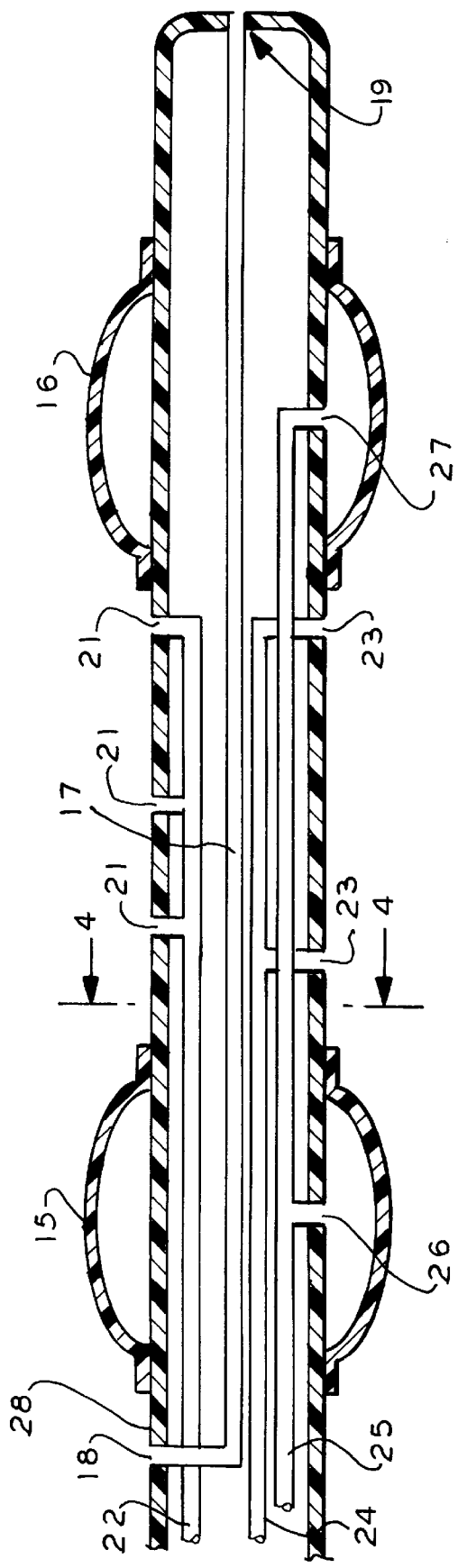
FIG. 3 is a cross sectional view of the double balloon catheter shown in FIG. 2.

With reference to the various Figs. of the drawing wherein like reference numerals denote like parts, there is illustrated in FIGS. 1 and 2 a front end or head end portion of a double balloon catheter that is positioned in a blood vessel or a major vein 10 such as a section of vena cava. Blood vessel groups 11, 12 and 13 each represent tributary veins that deliver blood to the major vein or vena cava which then returns blood to the heart. For purposes of this description, that group of tributary veins identified by reference numeral 11 are designated as those that carry blood from an organ such as a kidney to the vena cava while the other groups of tributary veins identified by reference numerals 12 and 13 are designated as those that deliver blood to the major vein or vena cava 10 from other parts of the host body.

The catheter head end portion includes inflatable devices which are preferably inflatable balloons, such as 15 and 16, and which are spaced from each other. In FIG. 1, balloons 15 and 16 are shown in a relaxed or deflated condition while in FIG. 2, they are shown in an inflated or expanded condition as 15a and 16a. Thus, balloons 15 and 16 are devices that can be inflated to 15a and 16a so as to form a blockage in the vessel in which the catheter is positioned as illustrated in FIG. 2.

When either the posterior balloon 15 or the anterior balloon 16 are in an expanded or inflated condition as 15a and 16a, a positive contact is made between the exterior walls of the balloons 15a, 16a and the internal wall of the major vein thereby forming a blockage in the vein 10. When both the posterior balloon 15a and the anterior balloon 16a are inflated or expanded as shown in FIG. 2, the major vein or vena cava 10 is blocked and an isolated section 10a is created between the two inflated balloons. Inflated balloons 15a and 16a form an enclosed and isolated section 10a in the major vein or vena cava spanning the entry points of the tributary veins 11 so as to capture and contain blood entering the isolated section 10a of the major vein or vena cava from the tributary veins 11. This blockage causes an interruption of the flow of blood through the major vein or vena cava.

To overcome and by-pass this interruption of blood flow, a blood shunt is provided. The blood shunt consists of an internal conduit or lumen 17 that is contained within and co-extends longitudinally along the interior of the double balloon catheter between the extremities of balloons 15 and 16. Internal conduit or lumen 17 has openings 18 and 19 formed therein at its outer ends that extend beyond balloons 15 and 16 as shown in FIGS. 2 and 3. In this manner, the blood shunt not only guarantees the integrity of the isolated section 10a in the major vein, but also provides an alternate path for the flow of blood past isolated section 10a thereby maintaining a continuous and uninterrupted flow of blood through vein 10.

Figure 5:
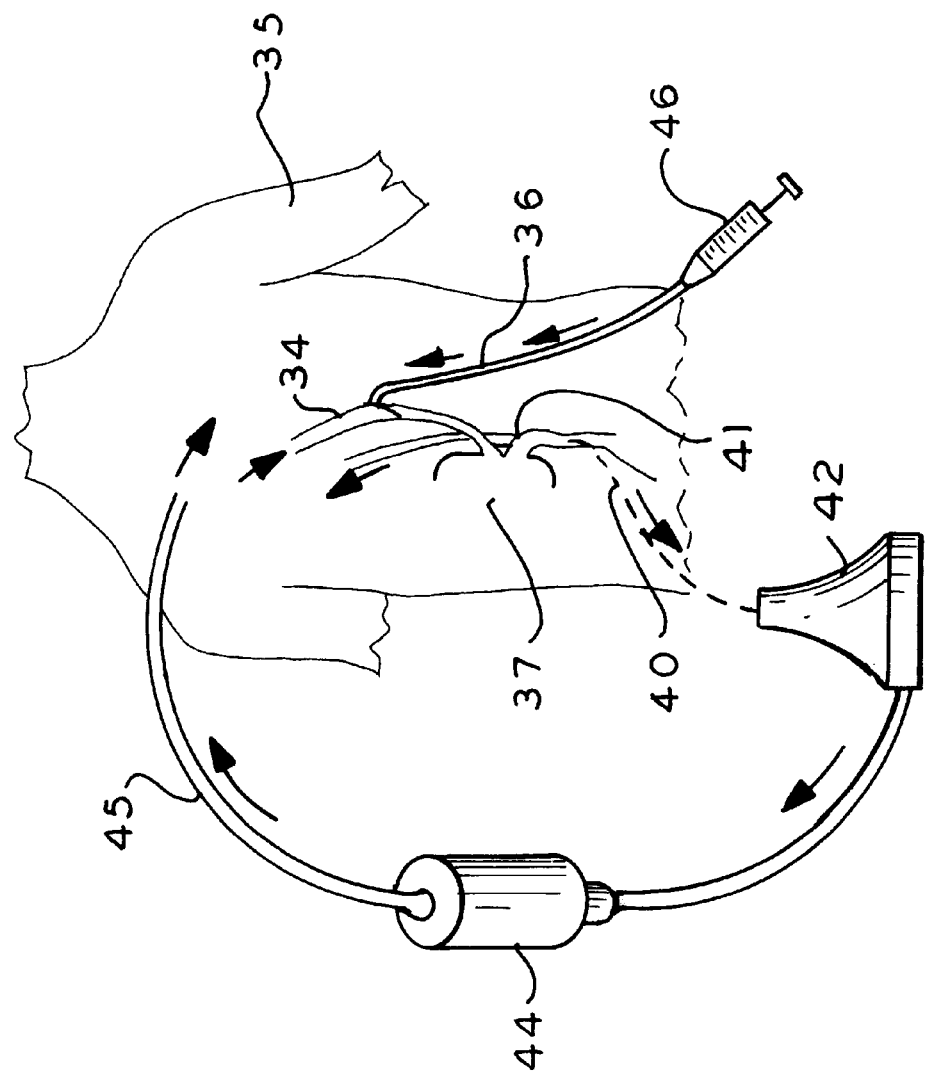
FIG. 5 is a schematic illustration of the instrumentation and devices that can be used in practicing the invention.
Figure 4:
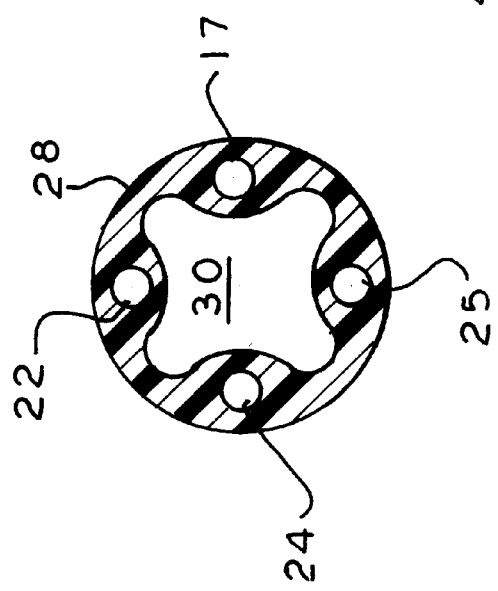
FIG. 4 is a view taken on line 4—4 of FIG. 3.

Inflating and deflating balloons 15 and 16 can be accomplished using well known and commonly accepted medical techniques and devices such as those that are capable of supplying a fluid to and evacuating a fluid from the interiors of these balloons by means of conduit or lumen 25 as illustrated in FIGS. 3 and 4. Conduit or lumen 25 is provided with ports 26 and 27 which communicate with the interiors of balloons 15 and 16. Conduit or lumen 25 is also longitudinally co-extensive with and contained within the interior of the double balloon catheter with the outer end of conduit or lumen 25 connected to an external control 42 as depicted in FIG. 5.

Additional conduits or lumens 22 and 24 are also contained within and are longitudinally co-extensive with the double balloon catheter extending to the outer end of the double balloon catheter. Conduits or lumens 22 and 24 can be provided with one or more openings 21 and 23 formed therein that communicate with the interior of the double balloon catheter as depicted in FIG. 3. Conduits or lumens 22 and 24 can be used for either infusion or evacuation purposes, but in the process of this invention, they are used to evacuate blood from the isolated section 10a of the major vein or vena cava. Conduit or lumen and opening combinations 21/22 and 23/224 can be used separately or in combination depending upon the velocity of blood flowing through the tributary veins 11.

The anterior of the double balloon catherer is positioned in the major vein or vena cava so that balloons 15 and 16 span that section in the major vein 10 where the tributary veins connect with the major vein. When balloons 15 and 16 are expanded to their inflated condition 15a and 16a, an isolated section 10a is created in the major vein between inflated balloons 15a and 16a so that blood entering the isolated section is captured and contained therein. The captured and contained blood can then be evacuated from the isolated section 10a through opening(s) 21 in conduit or lumen 22 and/or through opening(s) 23 and conduit or lumen 24 through the outer end of the double balloon catheter while blood is permitted to flow through the major vein by means of blood shunt 17 and ports 18 and 19.

FIG. 4 illustrates the outer wall 28 of the double balloon catheter with internal conduits or lumens 17, 22, 24 and 25 positioned therein. The central, internal portion 30 of the double balloon catheter is open along its longitudinal length so that a guide wire (not shown) can be inserted into central portion 30 to enable the double balloon catheter to be slid along its length in positioning the double balloon catheter in the circulation system as is typically practiced in current medical procedures.

FIG. 5 schematically illustrates conventional, external instrumentation that can be used with a host body 35 in practicing the process of the invention. A catheter, such as one used to deliver or evacuate fluids to or from internal parts of the body through arteries or veins of the circulation system, is inserted into an artery 34 between the heart and the organ, such as a kidney, 37 to be treated. A small incision is made in the body 35 so that a guide wire preferably made from stainless steel can be inserted into the body and fed along an artery 34 in the same direction as the blood is flowing in the artery to the organ 37. This is typically accomplished under observation through fluoroscopic instrumentation.

After the guide wire has been placed in position, the outer end of the guide wire outside the body is placed into the open end of a catheter 36 which is then slid along the guide wire into the body thence through the artery and positioned in the artery to enable a therapeutic agent to be infused and delivered through the catheter into the blood entering the organ 37. A therapeutic agent delivery means, represented by syringe 46, is connected to the outer end of the catheter to execute delivery of the therapeutic agent to the organ 37 to be treated.

A second small incision is made in the body 35 so that a second guide wire can be inserted into the body and fed along a major vein 41 in the same direction that blood is flowing in the major vein 41 to the organ 37 to be treated. After the second guide wire has been properly positioned, the outer end of the second guide wire is placed into the open center of a stiff bodied catheter having a top tapered to a point and tightly fitted to the guide wire. The body of this stiff bodied catheter is encased in a tightly fitting, thin walled sheath. This catheter combination is advanced into the vein over the second guide wire and the double balloon catheter of the invention is then slid along the second guide wire into the body through a major vein and into position at the organ 37 to be treated.

The major vein 10 with associated tributary veins 11 depicted in FIGS. 1 and 2 represent a like section of the major vein 41 shown in FIG. 5 in which tributary veins from the organ 37 to be treated connect with the major vein. In FIG. 5, the second catheter 40 represents the double balloon catheter with interior blood shunt and interior conduits and lumens shown in FIGS. 1, 2 and 3. Catheter 40 is inserted into a major vein 41 carrying blood from the organ 37 to be treated and from other body parts to the heart of the body and is positioned substantially as shown in FIGS. 1 and 2; that is, with balloons 15 and 16 effectively spanning the tributary veins 11 carrying blood from the organ 37 to the major vein. Proper positioning of the double balloon catheter 40 can be typically accomplished using fluoroscopic observation. When placed in major vein 41, double balloon catheter 40 spans the tributary veins 11 from the organ 37 so that blood flowing from the organ 37 can be captured and contained in the isolated section 10a of the major vein 41 when balloons 15 and 16 are inflated and expanded to 15a and 16a creating the isolated section 10a in the major vein 41 that contains the tributary veins 11.

At its outer end, double balloon catheter 40 is connected to a control 42 which is capable of inflating and deflating balloons 15 and 16. Control 42 also includes means for evacuating blood from the isolated section 10a in the major vein 41 through internal conduits or lumens 22 and 24 and their associated openings 21 and 23, respectively. The evacuated blood is fed to a filtering device 44 which removes contaminants and toxins from the blood and then returns the cleaned, detoxified blood to the body via conduit 45 which is inserted into the general circulation system of the body 35.

Just before or concurrently with the introduction of a therapeutic agent through catheter 36 by delivery means 46, control 42 is activated to cause both balloons 15 and 16 of the double balloon catherer 40 to expand to their inflated condition 15a and 16a securely contacting the interior wall of the major vein (FIG. 2). Balloons 15 and 16 are inflated sufficiently so as to be held firmly against the interior wall of the major vein 41 and form anterior and posterior blockages 15a and 16a therein. These blockages 15a, 16a create isolated section 10a and bracket or span tributary veins 11 from organ 37 enabling effluent blood from organ 37 to be captured and maintained in isolated section 10a until subsequently evacuated. Although this blockage is formed in the major vein 41, blood continues to flow through the major vein 41 from organ 37 by means of the blood shunt spanning the blocked portion of the vena cava.

In practicing the process of the invention, a therapeutic agent such as a biological agent and/or IL-2, for example, can be infused into the organ 37 to be treated via the blood flowing into the organ. This blood, after being contaminated with the therapeutic agent, can then be isolated and captured, evacuated from the body, cleansed, and then returned to the body. Meanwhile, normal blood flowing to the rest of the body is continued and maintained by means of the blood shunt by-pass.

Although the invention has been described with particularity and in some detail, it will be appreciated that modifications can be made therein as may become apparent to those skilled in the art without departing from the scope of the invention.

What is claimed is:

1. A method for in situ treatment of a kidney of a living body having a disease or tumor comprising:
   a) subjecting a kidney of a living body having a disease or tumor to an effective amount of a therapeutic agent by infusion of said agent via blood entering the kidney;
   b) creating an isolated section in a major vein spanning the area where the tributory veins connect with the major vein, the major vein and the tributary veins being directly associated with the kidney;
   c) passing contaminated effluent blood from the tributory veins of the kidney to said isolated section and capturing said effluent blood therein;

d) concurrently maintaining a continuous flow of blood through the major vein by directing said blood flow through a shunt in the major vein which shunt by-passes said isolated section; and, e) evacuating said captured blood from said isolated section without exposing said contaminated effluent blood to other organs or tissues of the living body and without interrupting the general blood circulation in the system of the living body.

2. The method of claim 1 wherein said isolated section is created by inserting a catheter having spaced expandable means in the major vein such that said spaced expandable means forms said isolated section.

3. The method of claim 1 wherein one of said spaced expandable means prevents said captured blood from flowing to the heart of the living body.

4. A method for the in situ treatment of a kidney of a living body having a disease or tumor comprising:

a) subjecting a kidney of a living body having a disease or tumor to an effective amount of a therapeutic agent by infusion of said agent via blood entering the kidney;

b) inserting a catherer having spaced expandable means in a major vein such that said spaced expandable means creates an isolated section in the major vein spanning the area where the tributory veins connect with the major vein, the major vein and the tributory veins being directly associated with the kidney;

c) passing contaminated effluent blood from the tributory veins of the kidney to said isolated section and capturing said effluent blood therein;

d) concurrently maintaining a continuous flow of blood through the major vein by directing said blood flow through a shunt in the major vein that by-passes said isolated section; and, e) evacuating said captured blood from said isolated section without exposing said effluent contaminated blood to other organs or tissues of the living body and without interrupting the general blood circulation in the system of the body.

5. The method of claim 4 wherein one of said spaced expandable means prevents said captured blood from flowing to the heart of the living body.

6. A method for in situ treatment of a kidney of a living body having a disease or tumor comprising:

a) subjecting a kidney of a living body having a disease or tumor to an effective amount of a therapeutic agent by infusion of said agent via blood entering the kidney, said therapeutic agent being a member selected from the group consisting of IL-2 and biological agents produced from recombinant DNA;

b) inserting a catheter having spaced, expandable means in a major vein such that said spaced expandable means creates an isolated section in the major vein where the tributory veins connect with the major vein, the major vein and the tributory veins being directly associated with the kidney, one of said spaced expandable means preventing said captured blood from flowing to the heart of the living body;

c) passing contaminated effluent blood from the tributory veins of the kidney to said isolated section and capturing said effluent blood therein;

d) concurrently maintaining a continuous flow of blood through the major vein by directing said blood flow through a shunt in the major vein that by-passes said isolated section; and, e) evacuating said captured blood from said isolated section without exposing said effluent contaminated blood to other organs or tissues of the living body and without interrupting the general blood circulation in the system of the living body.

\* \* \* \* \*

UNITED STATES PATENT AND TRADEMARK OFFICE
CERTIFICATE OF CORRECTION

PATENT NO.    : 6,186,146 B1
DATED         : February 13, 2001
INVENTOR(S)   : Morton Glickman It is certified that error appears in the above-identified patent and that said Letters Patent is hereby corrected as shown below:

<u>Title page,</u>
Below item [76] Inventor, insert the following:

-- [73]   Assignee: Delcath Systems, Inc., Stamford, CT (US) --.

Signed and Sealed this

First Day of April, 2003

JAMES E. ROGAN
*Director of the United States Patent and Trademark Office*